US012083134B2

(12) United States Patent
Sriram (10) Patent No.: US 12,083,134 B2
(45) Date of Patent: Sep. 10, 2024

(54) ANACARDIC ACID FOR NEURAL REPAIR (71) Applicant: Vanderbilt University, Nashville, TN (US)

(72) Inventor: Subramaniam Sriram, Nashville, TN (US)

(*) Notice: Subject to any disclaimer, the term of this patent is extended or adjusted under 35 U.S.C. 154(b) by 728 days.

(21) Appl. No.: 17/267,608

(22) PCT Filed: Aug. 12, 2019

(86) PCT No.: PCT/US2019/046119
§ 371 (c)(1),
(2) Date: Feb. 10, 2021

(87) PCT Pub. No.: WO2020/033943
PCT Pub. Date: Feb. 13, 2020

(65) Prior Publication Data
US 2021/0308152 A1 Oct. 7, 2021

Related U.S. Application Data (60) Provisional application No. 62/717,051, filed on Aug. 10, 2018.

(51) Int. Cl.
*A61K 31/60* (2006.01)
*A61P 25/28* (2006.01)

(52) U.S. Cl.
CPC .............. *A61K 31/60* (2013.01); *A61P 25/28* (2018.01)

(58) Field of Classification Search
CPC ....................................................... A61P 25/28
See application file for complete search history.

(56) References Cited

U.S. PATENT DOCUMENTS

| 5,240,962 | A | 8/1993 | Nakatsu |
| 2011/0250303 | A1 | 10/2011 | Nagashima |
| 2015/0045330 | A1 | 2/2015 | Inoue |
| 2017/0095436 | A1 | 4/2017 | Bjornsson |
| 2017/0107218 | A1 | 4/2017 | Zhou |
| 2017/0362231 | A1 | 12/2017 | Ibrahim |

FOREIGN PATENT DOCUMENTS

| JP | 08048621 A | 2/1996 |
| JP | 08291110 A | 11/1996 |
| JP | 09221473 A | 8/1997 |
| WO | 2016100858 A1 | 6/2016 |

OTHER PUBLICATIONS

Ljunggren-Rose, A. et al., PNAS, Sep. 1, 2020, vol. 117, No. 35, p. 21527-21535; printed from www.pnas.org/cgi/doi/10.1073/pnas. 2006566117 on Sep. 21, 2023.*
International Search Report and Written Opinion dated Nov. 1, 2019 for corresponding International Application No. PCT/US19/46119.
National Center for Biotechnology Information. "PubChem Compound Summary for CID 167551, Anacardic acid" PubChem, https://pubchem.ncbi.nlm.nih.gov/compound/Anacardic-acid. Accessed Jan. 21, 2021. https://pubchem.ncbi.nlm.nih.gov/compound/167551.
Reich, Daniel S et al. "Multiple Sclerosis." The New England journal of medicine vol. 378,2 (2018): 169-180. doi:10.1056/NEJMra1401483.
Noseworthy, J H et al. "Multiple sclerosis." The New England journal of medicine vol. 343,13 (2000): 938-52. doi:10.1056/NEJM200009283431307.
Wingerchuk, Dean M et al. "The spectrum of neuromyelitis optica." The Lancet. Neurology vol. 6,9 (2007): 805-15. doi:10.1016/S1474-4422(07)70216-8.
Rovaris, M., et al., "Secondary progressive multiple sclerosis: current knowledge and future challenges." he Lancet. Neurology vol. 5,4, (2006): 343-54.
Compston, Alastair, and Alasdair Coles. "Multiple sclerosis." Lancet (London, England) vol. 372,9648 (2008): 1502-17. doi:10.1016/S0140-6736(08)61620-7.
Franklin, Robin J M, and Charles Ffrench-Constant. "Remyelination in the CNS: from biology to therapy." Nature reviews. Neuroscience vol. 9,11 (2008): 839-55. doi: 10.1038/nrn2480.
Mahad, Don H et al. "Pathological mechanisms in progressive multiple sclerosis." The Lancet. Neurology vol. 14,2 (2015): 183-93. doi:10.1016/S1474-4422(14)70256-X.
Carvalho, Ana Laura Nicoletti et al. "Acute, subacute toxicity and mutagenic effects of anacardic acids from cashew (*Anacardium occidentale* Linn.) in mice." Journal of ethnopharmacology vol. 135,3 (2011): 730-6. doi:10.1016/j.jep.2011.04.002.
Balasubramanyam, Karanam et al. "Small molecule modulators of histone acetyltransferase p300." The Journal of biological chemistry vol. 278,21 (2003): 19134-40. doi:10.1074/jbc.M301580200.
Hemshekhar, Mahadevappa et al. "Emerging roles of anacardic acid and its derivatives: a pharmacological overview." Basic & clinical pharmacology & toxicology vol. 110,2 (2012): 122-32. doi:10.1111/j.1742-7843.2011.00833.x.
Philip, Joseph Y N et al. "Isolation of anacardic acid from natural cashew nut shell liquid (CNSL) using supercritical carbon dioxide." Journal of agricultural and food chemistry vol. 56,20 (2008): 9350-4. doi:10.1021/jf801532a.
Trevisan, M T S et al. "Characterization of alkyl phenols in cashew (*Anacardium occidentale*) products and assay of their antioxidant capacity." Food and chemical toxicology : an international journal published for the British Industrial Biological Research Association vol. 44,2 (2006): 188-97. doi:10.1016/j.fct.2005.06.012.

(Continued)

*Primary Examiner* — Gina C Justice
(74) *Attorney, Agent, or Firm* — Patterson Intellectual Property Law, P.C.; Mark A. Kilgore (57) ABSTRACT

Methods for stimulating neural repair and remyelination and for treating a myelin related disorder in a subject are described. The methods include administering to a subject in need of treatment an effective amount of anacardic acid having the formula (I) of claim 1 or a pharmaceutically acceptable salt thereof.

20 Claims, 9 Drawing Sheets

(56) References Cited

OTHER PUBLICATIONS

Natarajan, Chandramohan et al. "TLR3 Agonist Poly-IC Induces IL-33 and Promotes Myelin Repair." PloS one vol. 11,3 e0152163. (Mar. 29, 2016) doi:10.1371/journal.pone.0152163.

Sriram, S., et al., "IL-33 expression in MS: Role in Remyelination and repair." Neurology, 2016. Abstract presented at the American Academy of Neurology, 2016.

Bai, C Brian et al. "A mouse model for testing remyelinating therapies." Experimental neurology vol. 283, Pt A (2016): pp. 330-340. doi: 10.1016/j.expneurol.2016.06.033.

Deshmukh, Vishal A et al. "A regenerative approach to the treatment of multiple sclerosis." Nature vol. 502,7471 (2013): 327-332. doi:10.1038/nature12647.

Magalon, Karine et al. "Olesoxime accelerates myelination and promotes repair in models of demyelination." Annals of neurology vol. 71,2 (2012): 213-26. doi:10.1002/ana.22593.

Lassmann, Hans, and Monika Bradl. "Multiple sclerosis: experimental models and reality." Acta neuropathologica vol. 133,2 (2017): 223-244. doi: 10.1007/s00401-016-1631-4.

Satoh, M et al. "Synthesis of anacardic acids, 6-[8(Z), 11(Z)-pentadecadienyl]salicylic acid and 6-[8(Z), 11(Z), 14-pentadecatrienyl]salicylic acid." Chemical & pharmaceutical bulletin vol. 49,1 (2001): 18-22. doi:10.1248/cpb.49.18.

Swamy, M.M.M., et al., Structure-inspired design of a sphingolipid mimic sphingosine-1-phosphate receptor agonist from a naturally occurring sphingomyelin synthase inhibitor. Chem Commun (Camb), 2018. 54(90): p. 12758-12761.

Wisastra, R et al. "Discovery of a novel activator of 5-lipoxygenase from an anacardic acid derived compound collection." Bioorganic & medicinal chemistry vol. 21,24 (2013): 7763-78. doi: 10.1016/j.bmc.2013.10.015.

Wisastra, R et al. "Anacardic acid derived salicylates are inhibitors or activators of lipoxygenases." Bioorganic & medicinal chemistry vol. 20, 16 (2012): 5027-32. doi:10.1016/j.bmc.2012.06.019.

\* cited by examiner

Structure of anacardic acid with fully saturated side chain

Anacardic acid (AA)

Outline of mechanism of action of anacardic acid in remyelination

FIG. 2

MBP = myelin basic protein
Plp = proteolipoprotein
Mog = myelin oligodendrocyte glycoprotein

Increased expression of IL-33 in the presence of AA in OPCs

FIG. 5

Increased differentiation of OPCs to mature oligodendrocytes following culture with AA (Ana).

Enhanced Remyelination of Dorsal Root Ganglion cells by rIL-33

FIG. 9

Improved myelination in mice who were treated with 12.5 mg/kg AA daily after receiving cuprizone

Ability of AA to prevent EAE

FIG. 13

Progression of paralysis in mice treated with AA beginning from the earliest onset of paralytic signs

ANACARDIC ACID FOR NEURAL REPAIR

RELATED APPLICATIONS

This application claims the benefit of U.S. Provisional Application No. 62/717,051, filed Aug. 10, 2018, entitled "Anacardic Acid Neural Repair." This provisional application is hereby incorporated by reference in its entirety for all purposes.

BACKGROUND

Integrity of the central nervous system (CNS) is maintained by the appropriate connectivity between different regions of the neuraxis. This connectivity is maintained by the formation of myelin membranes which wrap around the axons and provide optimal transmission of electrical signals from the cortex to the different regions of the spinal cord. Oligodendrocytes in the central nervous system and Schwann cells in the peripheral nervous system (PNS) are the principal myelin producing cells and their integrity is essential for optimal nerve conduction. Diseases in which oligodendrocytes, Schwann cells, or myelin membranes are damaged can lead to neurological disability due to impaired conduction of electrical impulses.

Diseases of the myelin sheath can be classified as either dysmyelinating or demyelinating. In demyelinating diseases there is a breakdown of normal myelin sheaths, whereas in dysmyelinating diseases, normal myelin sheaths never form in sufficient quantities during nervous system development. Demyelinating disorders, which are usually acquired later in life, include immune and/or infectious conditions as well as those conditions resulting from traumatic injury (e.g. spinal cord injury).

Exposure to toxic chemicals (e.g. lead) or dietary deficiencies can present as either demyelinating or dysmyelinating disorders, depending on whether the environmental insult occurred early in development or after most myelin synthesis was complete. In humans, much of the myelin is laid down by 2 years of age, although some nerve tracts continue to accumulate sheaths well into the second decade of life. The most common cause of demyelination is from inflammatory diseases of the brain and spinal cord. Of these, multiple sclerosis (MS) is the best characterized disorder. Reich et al., N Engl J Med, 378(2):169-80 (2018); Noseworthy et al., New. Eng. J. Med, 343:938-46 (2000). The clinical course is characterized by episodes of neurological dysfunction (e.g. loss of motor control) followed by recovery, which can be monitored with magnetic resonance imaging to view the patches of disintegrating myelin (plaques) and the remyelinated regions. In addition, trauma to the brain and spinal cord also results in irreversible damage to myelin.

In demyelinating disorders of the CNS (Transverse myelitis, Devic's Disease, MS), failure of the body to remyelinate and repair the tissue damage appears to be a central feature of the disease and the cause of clinical disability. Wingerchuk et al., Lancet Neurol, 6(9): 805-15 (2007). This inadequate repair is evidenced in patients who do not recover from acute worsening of a demyelinating disorder of the CNS, patients who do not recover from an acute attack resulting in a demyelinating disorder, patients who show poor stabilization with regard to a progressive demyelinating disorder, and patients who are in the progressive phase of MS. Rovaris et al., Lancet Neurol, 5(4):343-54 (2006); Compston and Coles, Lancet, 372(9648): 1502-17 (2008); Franklin and French-Constant, Nat Rev Neurosci, 9(11): 839-55 (2008); Mahad et. al., Lancet Neurol, 14(2): 183-93 (2014).

SUMMARY OF THE DISCLOSURE

The development of novel therapeutics for the treatment of MS and other neurological disorders characterized by myelin loss or myelin deficiency is of great need. Current therapies for relapsing forms of MS have had limited impact on halting the progression of the disease because they do not address issues pertaining to neuro-repair, and in particular, remyelination. The present disclosure addresses these issues by providing methods for stimulating neural repair and remyelination and for treating myelin related disorders.

In one aspect, the present disclosure can include a method of stimulating neural repair in a subject in need thereof where the method includes administering to the subject an effective amount of anacardic acid (AA) of formula:

or a pharmaceutically acceptable salt thereof.

In another aspect, the present disclosure can include a method of stimulating remyelination in a subject in need thereof where the method includes administering to the subject an effective amount of AA or a pharmaceutically acceptable salt thereof.

Additionally, the present disclosure can include a method of treating a myelin related disorder in a subject in need thereof where the method includes administering to the subject an effective amount of AA or a pharmaceutically acceptable salt thereof.

In a further aspect, the myelin related disorder can include a disease, condition (e.g., those occurring from traumatic spinal cord injury and cerebral infarction), or disorder related to demyelination or remyelination in a subject. In some instances, the myelin related disorder can be a demyelinating disorder of the CNS. In one example, the demyelinating disorder can be MS. In another aspect, the myelin related disorder may be an autoimmune disorder that affects the function of the optic nerve, the brain, and/or the spinal cord.

In other instances, the subject has been diagnosed as having an infection causing demyelination. In one example, the infection causing demyelination can be a human immunodeficiency virus infection.

The present disclosure can also include compositions containing AA for use in stimulating neutral repair and remyelination and for treating a myelin related disorder. In some instances, the amount of AA that can be administered to a subject in accordance with the methods described herein can be between 250 mg and 1500 mg AA a day.

BRIEF DESCRIPTION OF THE FIGURES

The present disclosure may be more readily understood by reference to the following drawings, wherein:

FIG. 5 (top) provides the results of Western blot studies showing increased expression of IL-33 in the presence of AA in OPCs. FIG. 5 (bottom) shows image analysis of the gels indicating a 1.6 fold increase in protein expression. Because IL-33 is mainly in the nucleus, the Wester blots were done with nuclear extracts and Lamin was used as the control.

DETAILED DESCRIPTION OF THE DISCLOSURE

I. Definitions

The terminology as set forth herein is for description of the embodiments only and should not be construed as limiting of the disclosure as a whole. As used in the description of the disclosure and the appended claims, the singular forms "a", "an", and "the" are inclusive of their plural forms, unless contraindicated by the context surrounding such.

The disclosure is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the disclosure specifically includes each of the compound's enantiomers as well as racemic mixtures of the enantiomers. It should be understood that the term "compound" includes any or all of such forms, whether explicitly stated or not (although at times, "salts" are explicitly stated).

A subject, as defined herein, can be any animal. In one instance the subject is a vertebrate animal, and in a more particular instance the subject is a mammal, such as a domesticated farm animal (e.g., cow, horse, pig) or pet (e.g., dog, cat). In another instance, the subject is a human. The subject may also be a subject at risk of developing a myelin related disease.

As used herein, the term "treating" can relate to reversing, alleviating, inhibiting the progress of, or preventing a specific disorder or condition, prophylaxis of a specific disorder or condition, or alleviation of the symptoms associated with a specific disorder or condition and/or preventing or eliminating said symptoms.

"Pharmaceutically acceptable" as used herein means that the compound or composition is suitable for administration to a subject for the methods described herein, without unduly deleterious side effects in light of the severity of the disease and necessity of the treatment.

The term "therapeutically effective" is intended to qualify the amount of the agent that will achieve the goal of decreasing disease severity while avoiding adverse side effects such as those typically associated with alternative therapies. An "effective amount" on the other hand, is an amount sufficient to provide a significant chemical effect.

II. Overview

The present disclosure relates generally to methods for stimulating neural repair and remyelination and for treating myelin related disorders through the administration of AA.

The present disclosure is based, at least in part, on the finding that cytokine IL-33 is involved in myelin regeneration and repair. Based on this finding, strategies to increase cytokine IL-33 have been investigated including identification of therapeutic agents that may promote the expression of IL-33. It has been discovered that AA, which is a naturally occurring compound found in cashew fruits and shells, induces cytokine IL-33 in oligodendrocyte precursor cells (OPCs) and induces the expression of certain myelin genes in OPCs. Thus, AA is an attractive naturally occurring compound for neural repair.

Figure 1:
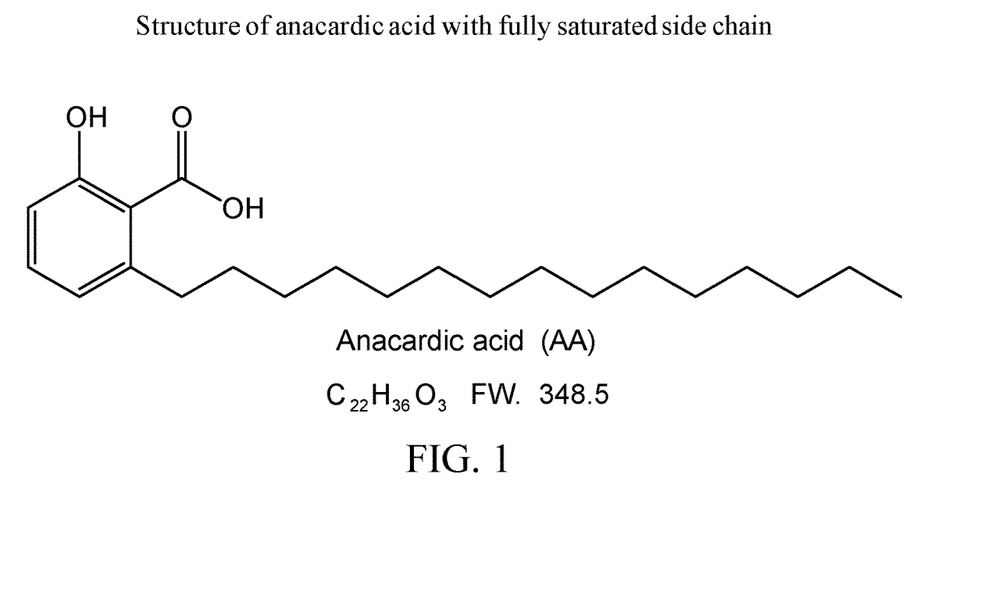
FIG. 1 shows the structure of anacardic acid (AA) with a fully saturated side chain.

AA is a non-isoprenoid long chain phenolic acid primarily obtained from the nut shells of the plant *Anacardium occidentale* that is native to South America. (FIG. 1).

AA

The solvent extracted cashew nut shell liquid (CNSL) is a rich source of many long chain phenolic compounds including various anacardic acids. There are three major anacardic acids found in CNSL. These three major forms are the monoene, the diene, and the triene. The fully saturated form, referred to as AA, is present in negligible amount. Taken together, the monoene, the diene, the triene, and AA are referred to herein as the natural anacardic acids ("NAAs").

Monoene

Diene

Triene

The NAAs are lipophilic small molecules making them particularly interesting for stimulating neural repair and remyelination because they have the capacity to enter the central nervous system, including the capacity to enter the brain when the blood brain barrier is intact. Although the instant disclosure refers to the use of AA for stimulating neural repair and remyelination, and for treating myelin related disorders, it should be understood that any of the NAAs can be used in the methods described herein.

Methods

One aspect of the disclosure provides a method of stimulating neural repair in a subject in need thereof, comprising administering to the subject an effective amount of AA or a pharmaceutically acceptable salt thereof. The disclosure also provides a method of stimulating remyelination in a subject in need thereof, comprising administering to the subject an effective amount of AA or a pharmaceutically acceptable salt thereof. Additionally, the present disclosure can include a method of treating a myelin related disorder in a subject in need thereof, where the method includes administering to the subject an effective amount of AA or a pharmaceutically acceptable salt thereof.

Myelin disorders can include any disease, condition (e.g., those occurring from traumatic spinal cord injury and cerebral infarction), or disorder related to demyelination or remyelination in a subject. The death of myelin forming cells may be due to trauma, toxins, lack of nutrition, genetic disorder, or an inflammatory disease involving either the CNS or PNS.

Demyelination is the hallmark of some neurodegenerative autoimmune diseases, including MS, transverse myelitis, chronic inflammatory demyelinating polyneuropathy, and Guillain-Barre Syndrome. Non-limiting examples of neurological disorders treatable by the methods described herein include MS (e.g., Relapsing/Remitting MS, Secondary Progressive MS, Progressive Relapsing MS, Primary Progressive MS, and Acute Fulminant MS), Central Pontine Myelinolysis, Acute Disseminated Encephalomyelitis, Progressive Multifocal Leukoencephalopathy, Subacute Sclerosing Panencephalitis, Post-infectious Encephalomyelitis, Chronic Inflammatory Demyelinating Polyneuropathy, Devic's Disease, Balo's Concentric Sclerosis, the leukodystrophies (e.g., Metachromatic Leukodystrophy, Krabbe disease, Adrenoleukodystrophy, Pelizaeus-Merzbacher disease, Canavan disease, Childhood Ataxia with Central Hypomyelination, Alexander disease, or Refsum disease), optic neuritis, transverse myelitis, cerebral palsy, spinal cord injury, age-associated myelin deficiency, as well as acquired and inherited neuropathies in the peripheral nervous system (e.g., Guillain-Barre Syndrome and Charcot Marie Tooth disease). In one example, the neurological disorder is MS.

In some instances, the subject has been diagnosed as having a demyelinating disorder of the CNS including those listed in Table 1.

TABLE 1

| Demyelinating disorders of the CNS | |
|---|---|
| Trauma to CNS | Contusion injury to spinal cord |
| Primary Demyelinating Disorders | Multiple Sclerosis |
|  | Neuromyelitis optica |
|  | Acute disseminated encephalomyelitis |
|  | Acute Transverse myelitis |
|  | Acute and Progressive optic Neuritis |
| Infections causing demyelination | Human Immunodeficiency Virus (HIV) |
|  | Human T Lymphocytic Virus-1 (HTLV-1) |
|  | Progressive multifocal leucoencephalopathy |
| Vascular insufficiency | Stroke |

In some instances, the subject has been diagnosed as having a primary demyelinating disorder. For example, the primary demyelinating disorder can be MS. In a further aspect, the subject has been diagnosed as having an infection causing demyelination. For example, the infection causing demyelination can be a human immunodeficiency virus infection.

In an additional aspect, the myelin related disorder may be an autoimmune disorder that affects the function of the optic nerve, the brain, and/or the spinal cord.

In another instance, the disclosure can include a method of preventing demyelination in a subject who has been shown to be at high risk for developing a demyelinating disorder. For example, an inflammatory demyelination disorder can be prevented by administering AA to the subject. Additionally, AA can be administered to a subject who is at high risk for stroke, a vascular injury, or traumatic injury by administering maintenance doses of AA to the subject to reduce the severity of any future myelin damage.

Methods for assessing neural repair and remyelination in a subject are known in the art. For example, conventional MRI, magnetization transfer (MT) imaging, myelin water fraction, diffusion tensor imaging (DTI), and positron emission tomography (PET) imaging can be used to assess neural repair and remyelination in a subject. In addition, biomarkers that reflect the presence of brain proteins, such as neurofilament light chain present in either the blood or spinal fluid, can be used to determine neurodegeneration.

Formulation and Administration of AA

The present disclosure provides a method for administering an AA compound in a pharmaceutical composition. Examples of pharmaceutical compositions include those for oral, intravenous, intrathecal, intramuscular, subcutaneous, or intraperitoneal administration, or any other route known to those skilled in the art, and generally involves providing an AA compound formulated together with a pharmaceutically acceptable carrier. In some instances, the AA compound may be incorporated into a hydrogel mesh or a scaffolding that may be implanted at the site of injury to provide a continuous release of AA at the injury site.

When preparing pharmaceutical compositions for oral administration, the pharmaceutical composition may be in the form of, for example, a tablet, capsule, suspension or liquid. The pharmaceutical composition is preferably made in the form of a dosage unit containing a particular amount of the AA compound. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The AA compound may also be administered by injection as a composition wherein, for example, saline, dextrose or water may be used as a suitable carrier.

For intravenous, intrathecal, intramuscular, subcutaneous, or intraperitoneal administration, the AA compound may be combined with a sterile aqueous solution which is preferably isotonic with the blood of the recipient. Such formulations may be prepared by dissolving the solid AA compound in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the AA compound which is preferably made isotonic. Preparations for injections may also be formulated by suspending or emulsifying the AA compound in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of AA compound that is administered, and the dosage regimen for treating a disease condition with the AA compound and/or compositions described herein may vary widely depending on a variety of factors, including the age, weight, sex, and medical condition of the subject, the severity of the disease, the route and frequency of administration, the particular AA compound employed, as well as the pharmacokinetic properties of the individual treated. The dosage will generally be lower if the AA compound is administered locally rather than systemically, and for prevention rather than for treatment. Such treatments may be administered as often as necessary and for the period of time judged necessary by the treating physician. For example, treatments may be administered daily, every other day, weekly, or monthly.

One of skill in the art will appreciate that the dosage regime or therapeutically effective amount of the AA compound to be administrated may need to be optimized for each individual. The pharmaceutical compositions may contain an AA compound in the range of about 0.1 to 2000 mg. For example, the AA compound may be present in the pharmaceutical composition in the range of about 0.5 to 1500 mg or in the range of about 1 to 200 mg. A daily dose of about 0.01 to 100 mg/kg body weight or about 0.1 to 50 mg/kg body weight of the AA compound may be appropriate. In one example, the daily dose of AA that is administered is between 250-1500 mg. In another example, the daily dose of AA that is administered is 675 mg. The daily dose can be administered in one to four doses per day.

The maximum tolerated dose (MTD) for an AA compound can be determined in tumor-free athymic nude mice. Agents are prepared as suspensions in sterile water containing 0.5% methylcellulose (w/v) and 0.1% Tween 80 (v/v) and administered to mice (7 mice/group) by oral gavage at doses of 0, 25, 50, 100 and 200 mg/kg once daily for 14 days. The body weights of the mice are measured twice weekly, and direct daily observations of general health and behavior serve as primary indicators of drug tolerance. MTD is defined as the highest dose that causes no more than 10% weight loss over the 14-day treatment period. Carvalho et al., J Ethnopharmacol, 135(3): 730-36 (2011).

The AA compound can be provided as pharmaceutically acceptable salt. The phrase "pharmaceutically acceptable salt" connotes salts commonly used to form alkali metal salts and to form addition salts of free acids or free bases. The nature of the salt is not critical, provided that it is pharmaceutically acceptable. Suitable pharmaceutically acceptable acid addition salts of the compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, γ-hydroxybutyric, galactaric, and galacturonic acids. Suitable pharmaceutically acceptable base addition salts of the AA compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

The AA compound may also be administered concurrently with other medications. For instance, the AA compound may be administered with steroid drugs such as prednisone, prednisolone, methylprednisolone, betamethasone, and dexamethasone. The AA active compound may also be administered with disease modifying drugs such as interferon beta-1a and interferon beta-1b containing drugs. In other instances, the AA compound may be administered with drugs such as glatiramer acetate, mitoxantrone, natalizumab, teriflunomide, fingolimod, alemtuzumab, dimethyl fumarate, and dalfampridine.

Preparation of AA Compounds

The AA compounds for use in the methods described herein may be synthesized by routes known in the art and processes analogous to those well known in the chemical arts, particularly in light of the description contained herein. Satoh, et al., Chem Pharm Bull (Tokyo), 49(1): 18-22 (2001); Swamy et al., Chem Commun (Camb), 54(90): 12758-61 (2018). AA and other starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.) and similar texts known to those skilled in the art.

The purification of anacardic acid, including cardols and cardonols, has been performed from cashew nut shell oil. The anacardic acid was isolated as the calcium salt and the acid free cashew nut shell liquid was treated with ammonia and extracted with hexane and ethyl acetate mixture. In addition, anacardic acid has been isolated from cashew nut shell oil using supercritical carbon dioxide which avoids the use of organic solvents. Balasubramanyam et al., J Biol Chem, 278(21): 19134-40 (2003); Hemshekhar et al., Basic Clin Pharmacol Toxicol, 110(2):122-32 (2012); Philip et al., J Agric Food Chem, 56(20):9350-54 (2008).

The present disclosure is illustrated by the following examples. It is to be understood that the particular examples, materials, amounts, and procedures are to be interpreted broadly in accordance with the scope and spirit of the disclosure as set forth herein.

EXAMPLES

Example I: AA as a Therapeutic Agent for Neural Repair and Remyelination

*Anacardium occidentale* (cashew), a member of the family Anacardiaceae, is a tropical tree indigenous to Brazil which is extensively cultivated in India and east Africa. Trevisan et al., Food Chem Toxicol, 44(2): 188-97 (2006). Cashew nut shell liquid (CNSL) is an important agricultural by-product of cashew nut shell. Anacardic acids constitute close to 70% of the ingredients present in the cashew shell liquid. Anacardic acids are phenolic lipids that are partially miscible with ethanol and ether, but nearly immiscible with water. Chemically, anacardic acids consist of a salicylic acid moiety substituted with an alkyl chain that has 15 or 17 carbon atoms that may be saturated or unsaturated. The long alkyl chain present on the anacardic acids gives the anacardic acids their lipophilic properties. Hemshekhar et al., Basic Clin Pharmacol Toxicol, 110(2): 122-32 (2012).

(i) Anacardic Acid (AA) Increase Myelin Gene Synthesis.

Figure 2:
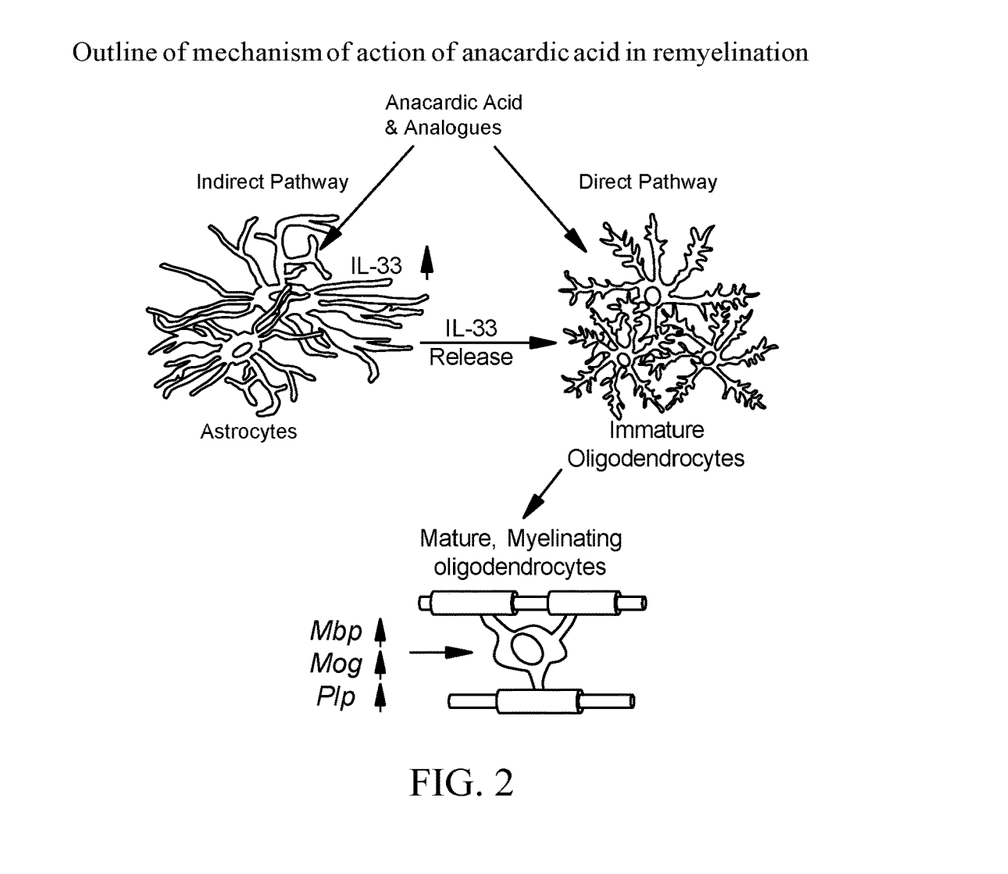
FIG. 2 shows the direct and indirect pathway, through induction of IL-33, for the activation of myelin genes in oligodendrocyte precursor cells (OPCs).
Figure 3:
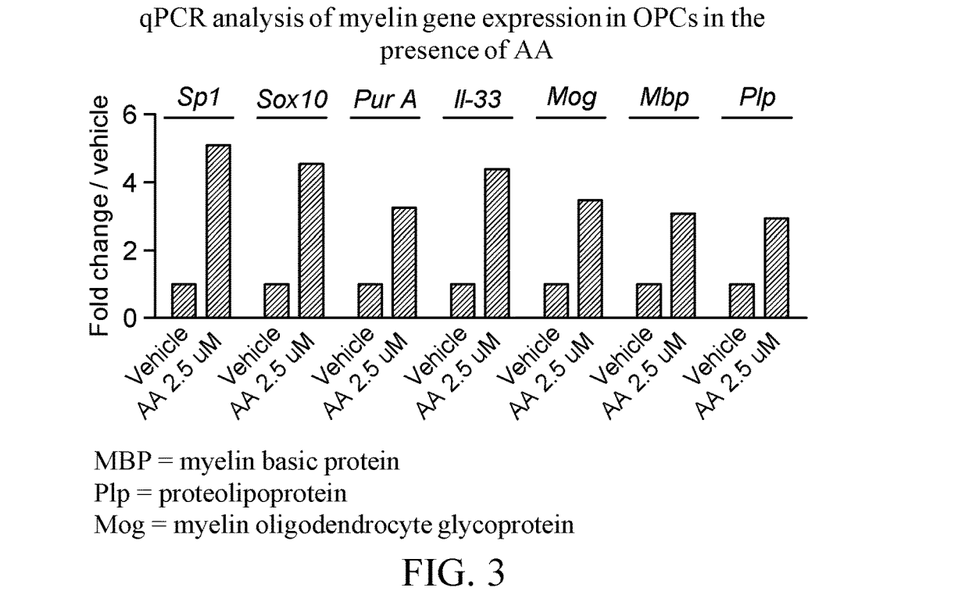
FIG. 3 shows the qPCR analysis of myelin gene expression in OPCs following the addition of AA. Mbp=myelin basic protein, Plp=proteolipoprotein, Mog=myelin oligodendrocyte glycoprotein.

The effect of AA on the expression of myelin genes, MBP, and IL-33 was examined. The induction of IL-33 in OPCs was pursued because of studies that were conducted that showed that IL-33 was a key inducer of myelin genes (FIG. 2). Natarajan et al., PLOS One, 11(3):e0152163 (2016); Sriram et al., Neurology, Abstract presented at the American Academy of Neurology, 2016 (2016). The studies were done in OPCs obtained from rat pups. OPCs were treated with AA (2.5 μM) for 3 hours and message levels were quantified using qPCR analysis. OPCs treated with AA induced the major myelin genes Mbp, Mog and Plp. In addition, qPCR analysis revealed the upregulation of the transcription elements Sp1, Sox10 and Purα that bind at the promoter region of Mbp (FIG. 3).

The expression of IL-33 induced by AA in OPCs was also examined. As shown in Table 2, there was an 8.54 fold increase in the expression of IL-33 in OPCs cultured for 3 hours in the presence of 2.5 μM AA. (FIG. 3). The data is expressed as fold change compared to the control protein GAPDH.

TABLE 2 q-PCR on the induction of IL-33 in OPCs cultured in the presence or absence of AA.

| 20 ng/cDNA | GAPDH (ct) | IL-33 (ct) | Fold change |
|---|---|---|---|
| Vehicle 3 h | 26.625 | 32.155 | 1.00 |
| AA 2.5 μM 3 h | 28.285 | 30.72 | 8.54 |
| AA 5 μM 3 h | 27.135 | 30.41 | 4.77 |

(ii) Induction of MBP in OPCs cultured with AA.

Figure 4:
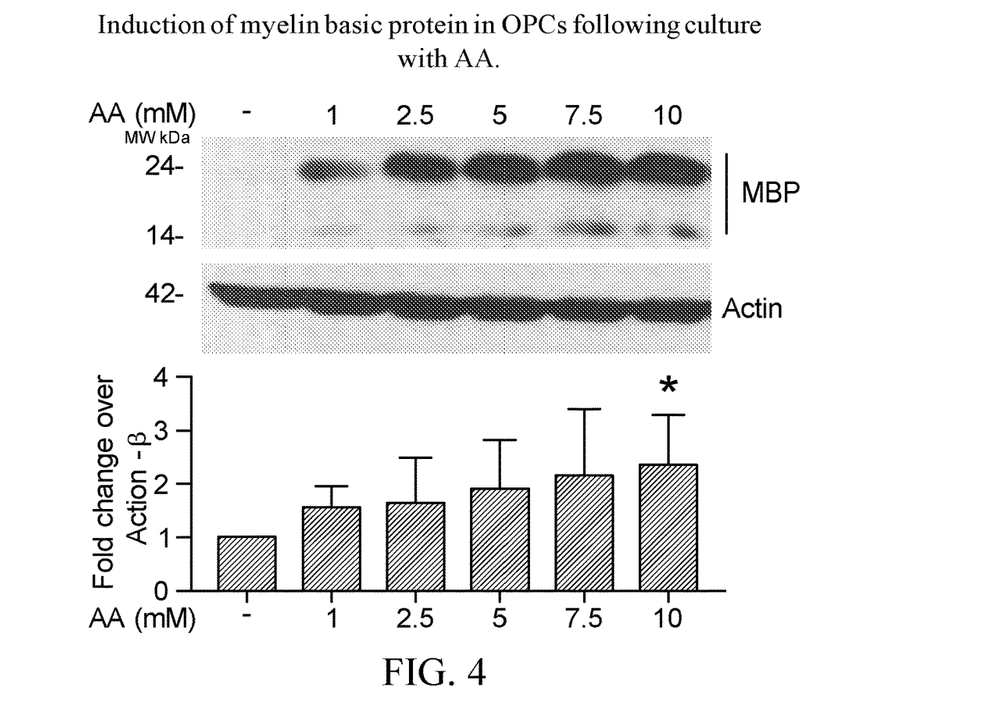
FIG. 4 (top) shows the induction of myelin basic protein (MBP) in OPCs following culture with AA. Image analysis (bottom) showed a 2.4 fold increase in the expression of MBP following culture with AA.

To further verify the ability of AA to induce MBP protein synthesis, $4 \times 10^6$ OPCs were cultured in poly-D lysine coated culture dishes with and without AA for 10 days. The AA concentrations that were studied were as follows: 1, 2.5, 5, 7.5, and 10 μM. The growth medium was changed every three days. OPCs from newborn pups did not express myelin proteins postnatal on day 0. Upon culture in vitro, OPCs differentiated and became myelin expressing cells, a process which took about 7-14 days. As anticipated, Western blot analysis revealed that AA treatment increased the level of MBP in a dose dependent manner (FIG. 4) suggesting that AA can act as a trophic factor for myelinogenesis.

Figure 5:
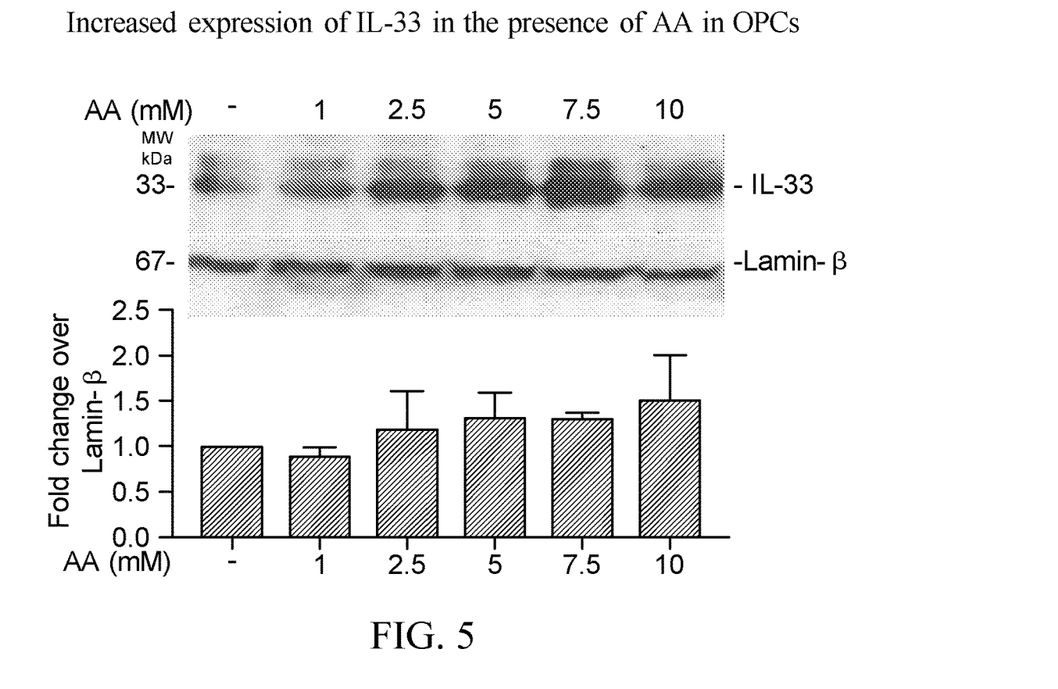

In addition, at a dose of 2.5 μM of AA, there was a 1.8 fold increase in the protein level of IL-33, and at a dose of 7.5 μM of AA, there was a 3.1 fold increase in the protein level of IL-33 (FIG. 5). These studies show that AA can induce MBP and MBP genes both directly and indirectly by the induction of IL-33.

(iii) AA Induces the Maturation of OPCs

Figure 6:
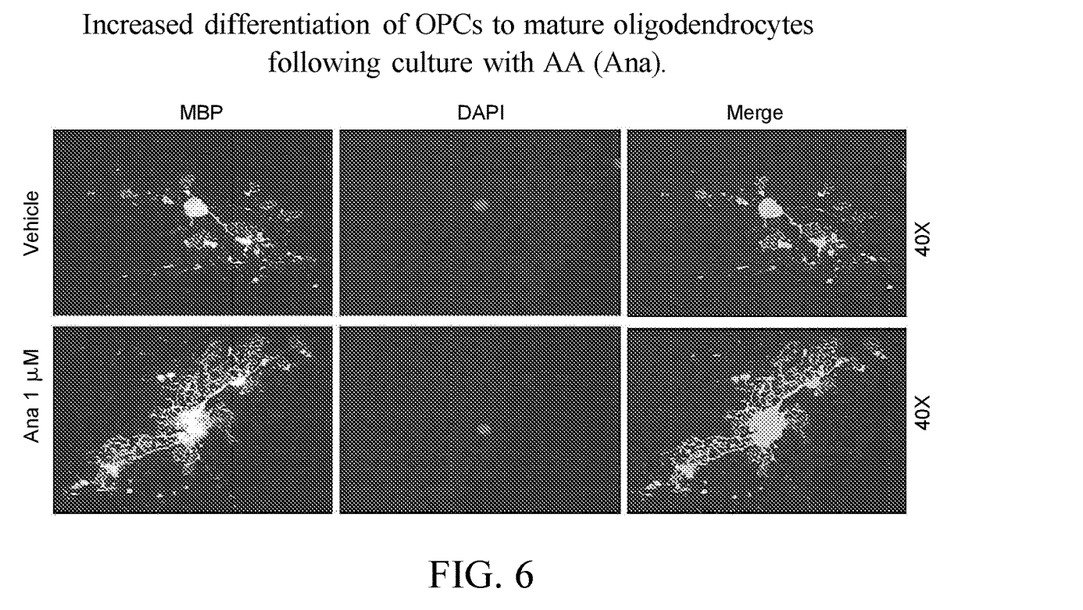
FIG. 6 provides images showing the increased differentiation of OPCs to mature oligodendrocytes following culture with AA (Ana). OPCs were isolated from rat pups and were cultured with AA where 1 µM of AA was added to the culture every other day for 14 days. At the end of the experiment, the cells were stained and the amount of MBP was assessed using ImagJ software.

The expression of MBP, a marker for myelin maturation in OPCs, was investigated in the presence and absence of AA (1 μM) following culture with AA for 14 days. As shown in FIG. 6, there was a 2.1 fold increase in the expression of MBP when compared to cells cultured in normal growth medium.

(iv) Induction of MBP and MBP Genes by IL-33 in OPCs in the Presence of AA.

Figure 7:
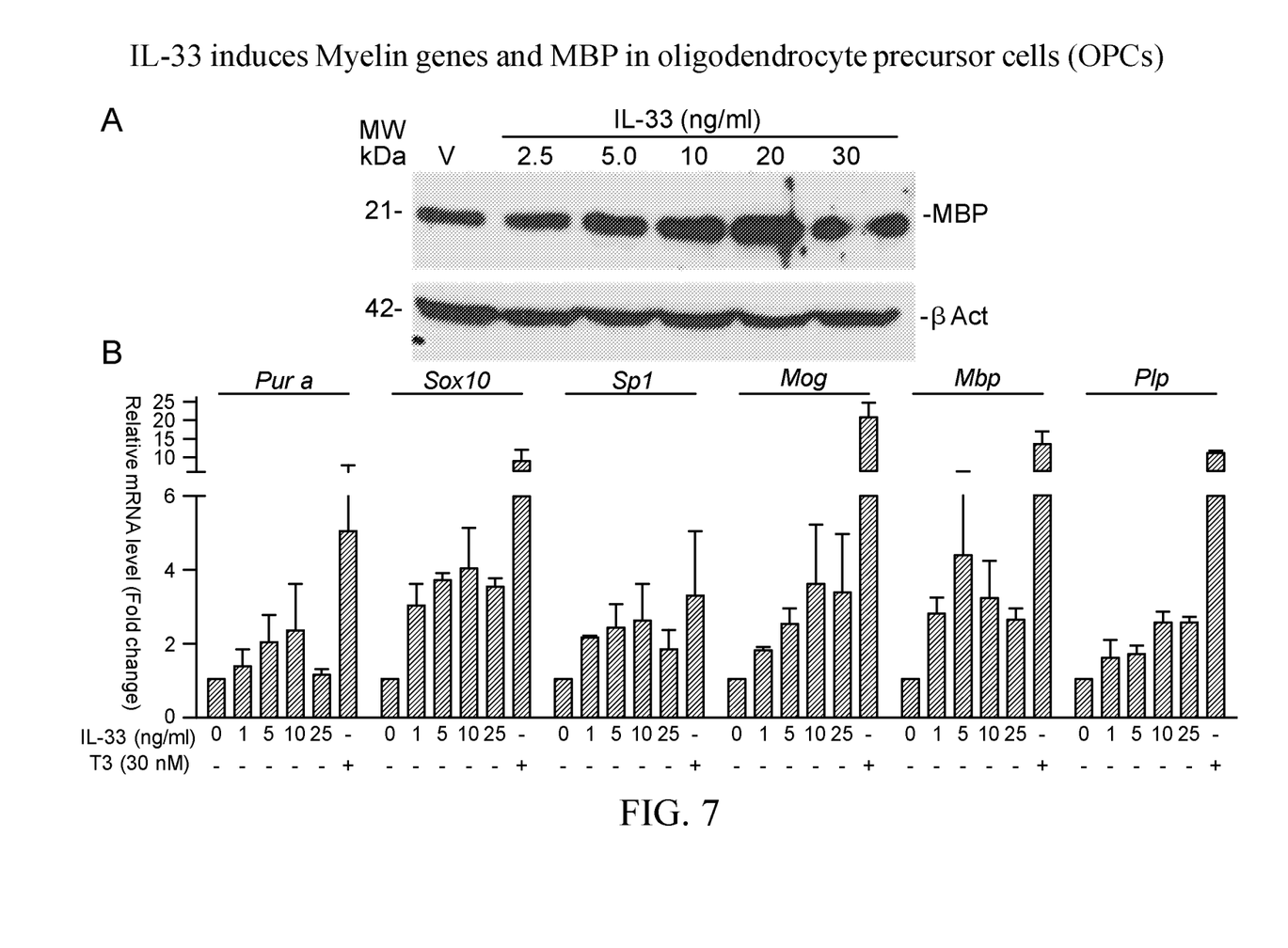
FIG. 7A provides Western blot analysis of MPB expression in OPC cultures treated with IL-33.
FIG. 7B provides qRT-PCR analysis showing the gene expression of transcription elements that bind to the MPB promoter region and major myelin genes treated with IL-33. T3 is the thyroid hormone internal positive control.

The importance of IL-33 as an inducer of a number of myelin genes has been shown. Treatment of OPCs with IL-33 showed a 26% induction of MBP. The expression of MBP, myelin oligodendrocyte glycoprotein (Mog), and proteolipoprotien (Plp) along with mRNAs of Purα, Sox10, and Sp-1 in OPCs cultured with IL-33 was quantified. Purα, Sox10, and Sp-1 are transcription elements that bind to the promoter region of MBP to initiate MBP gene expression. As shown in FIG. 7A, addition of IL-33 induced the expression of MBP by 4.5 fold, of Mog by 3.8 fold, of PLP by 2.3 fold, of Purα by 2.1 fold, of Sox10 by 3.9 fold, and of Sp1 by 2.2 fold. This data suggests that exogenous addition of recombinant IL-33 is an inducer of key genes involved in myelination (FIG. 7B).

(v) IL-33 Induces the Maturation of OPCs.

Figure 8:
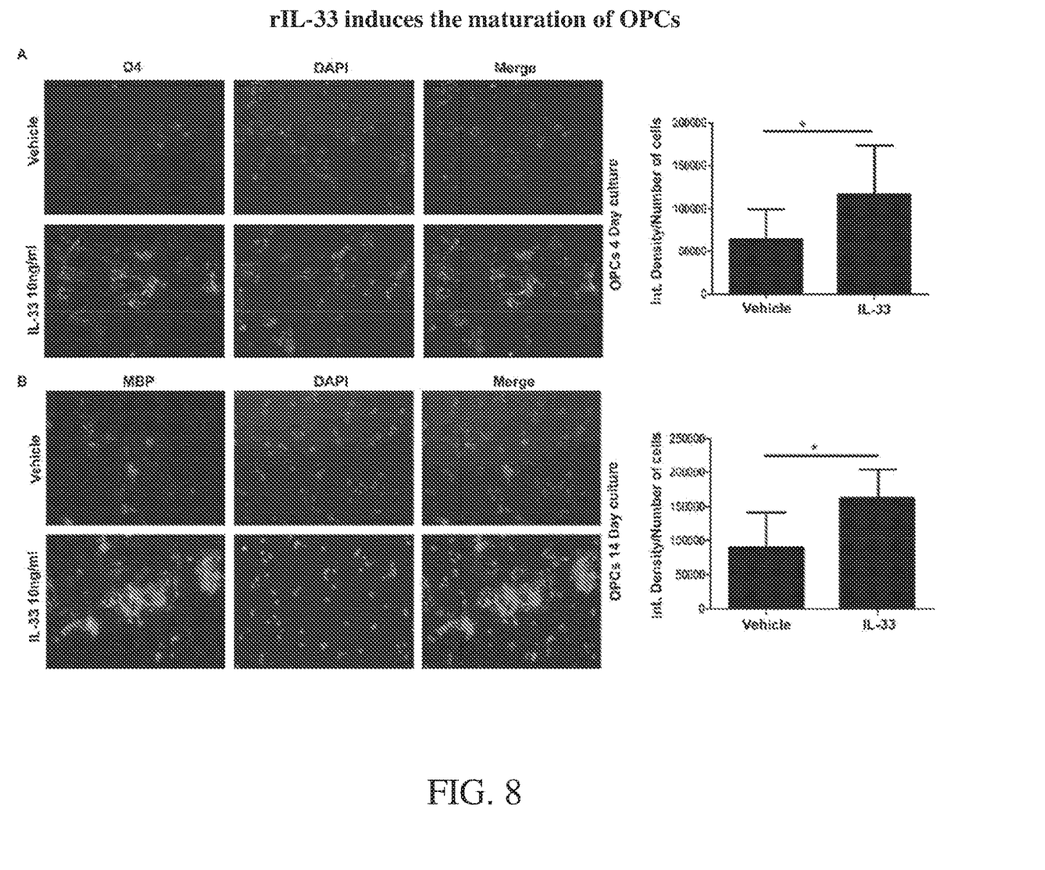
FIG. 8A shows the increase in the number of O4 expressing cells (early progenitor cells) on day 4 in the presence of IL-33 (upper set of panels).
FIG. 8B shows the increase in MBP expressing cells in OPC cultures on day 14 (lower set of panels). The graphs to the right show the quantitation of O4 and MBP.

The formation of CNS myelin is dependent on the differentiation and maturation of OPCs. The process of maturation is well recognized both in vitro and in vivo. Immature OPCs express the receptor for platelet derived growth factor (PDGFR) and also express proteins that are recognized by antibody A2B5, anti O4, and anti Olig2 antibodies. As oligodendrocytes mature they lose their reactivity to A2B5, PDGFR, and Olig 2 and they begin to express myelin proteins including MBP. The degree of maturation can be assessed by determining the percentage of cells expressing early lineage markers such as O4 and the later markers such as MBP. The expression of O4 and MBP in OPCs cultured for 4 and 14 days in the presence or absence of IL-33 was determined. As shown in FIG. 8A, there was a 2.3 fold increase in the expression of O4 expressing cells cultured with IL-33 after 4 days when compared to cells cultured in normal growth medium. When the OPCs were cultured for 14 days, there was increased formation of mature oligodendrocytes into a membranous form expressing high levels of MBPs (FIG. 8). The increase seen with IL-33 was similar to that seen with AA.

(vi) IL-33 Induces Myelination of Axons.

Figure 9:
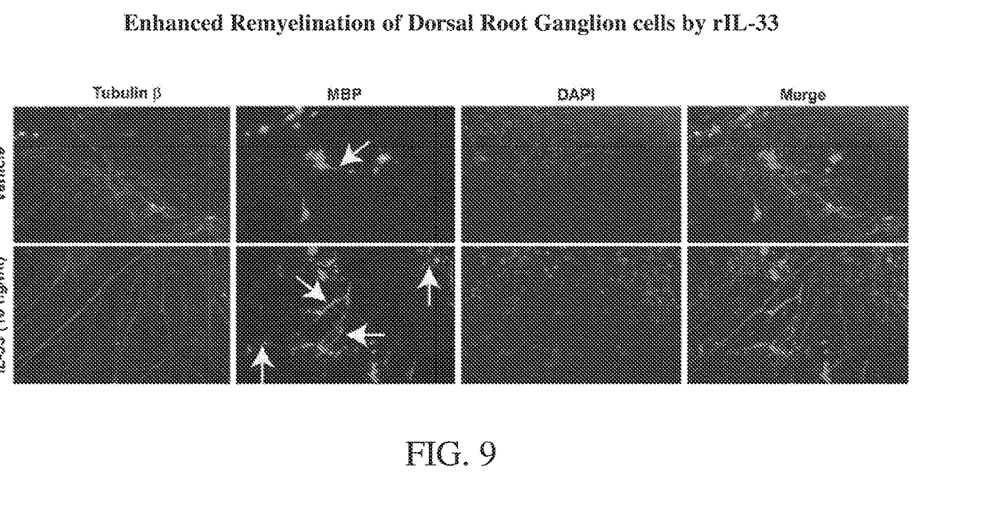
FIG. 9 provides images showing the myelination of dorsal root ganglion axons. The arrows point to the longer segments of myelinated internodes in cultures with added IL-33 (20×).

In preliminary studies, in vitro myelination of axons in the presence of IL-33 using dorsal root ganglia-OPC co-cultures was examined. Dorsal root ganglions (DRGs) were dissected from postnatal day 2 (P2) rat pups and cultured by established methods. Once the OPCs attached to the plates, they were treated with rat rIL-33 (10 ng/ml) for 16 days. At the end of the experiment, cells were stained with tubulin β for axons and MBP for myelin forming oligodendrocytes. Quantitation of myelin in axons was done using image analysis and the amount of myelin around the axons was determined. Addition of IL-33 resulted in increased myelination of naked axons. When compared to vehicle treated controls, there was an 18% increase in MBP in cultures treated with IL-33. These studies suggest that exogenous addition of recombinant IL-33 induces expression of key proteins involved in myelination (FIG. 9).

(vii) AA is Effective in Inducing Myelination in the Cuprizone Induced Model of Demyelination.

The cuprizone induced model of demyelination is a model for toxic demyelination. Torkildsen et al., Acta Neurol Scand Suppl. 188:72-6 (2008); Bai et al., Exp Neurol, 283(Pt A): 330-40 (2016). Cuprizone induces extensive demyelination in large white matter tracts of the CNS. Because the corpus callosum is the largest white matter tract in the brain, it is often used to study demyelination/remyelination in the cuprizone model. In the cuprizone model, animals are fed with cuprizone that causes cell death of oligodendrocytes. However, because cuprizone does not destroy new oligodendrocytes, remyelination occurs during and following cuprizone-induced demyelination. Furthermore, removal of cuprizone from the diet of animals has been shown to result in the rapid remyelination of axons. Deshmukh et al., Nature, 502(7471):327-32 (2014); Magalon et al., Ann Neurol, 71(2):213-26 (2012). Since the model is non-immune mediated, neuro-reparative therapies which promote remyelination can be tested without the interference of markers of inflammation. Lassmann and Bradl, Acta Neuropathol, 133 (2):223-44 (2017).

In order to demonstrate a therapeutic effect using the cuprizone induced model of demyelination, the drug has to promote remyelination to a greater degree than the degree of remyelination that would otherwise occur naturally. The efficacy of any potential drug is only apparent for a short period of time after cuprizone withdrawal and before the natural process of remyelination catches up. Following cuprizone withdrawal, there is complete remyelination after 6 weeks. Thus, a study was conducted where mice were administered cuprizone in their chow for nine weeks and either AA or a vehicle were administered with the cuprizone starting at 7 weeks. Previous studies have shown that chow mixed with 0.2% cuprizone causes wide spread demyelination and demyelination is seen in the corpus callosum after 6 to 8 weeks on cuprizone. At the beginning of week 7, mice received 12.5 mg/kg of AA dissolved in DMSO sc daily for an additional three weeks. Control mice received an equal volume of DMSO (vehicle). Equal numbers of mice (5/group) were sacrificed and the amount of myelin was determined by staining with luxol fast blue ("LFB") (chemical stain for myelin) or by staining with anti MBP antibodies at the end of weeks 7, 8 and 9. Representative samples of mice were sacrificed at the end of weeks 7, 8 and 9 and the corpus callosum was then examined for demyelination. Representative sections were stained from two regions of the corpus callosum, 5 mm apart. The summary of the results is shown below.

Figure 10:
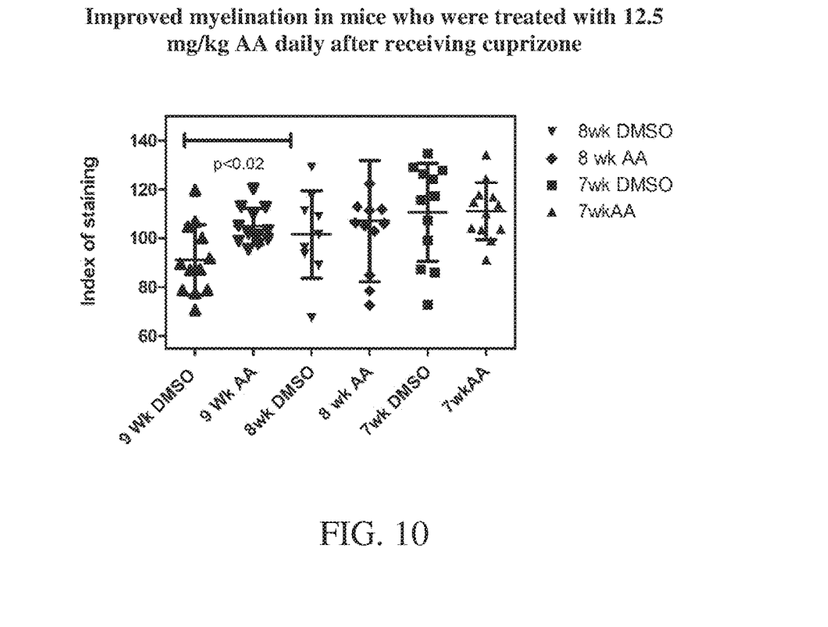
FIG. 10 shows the improved myelination in mice in a 9-week study. Mice were administered cuprizone for nine weeks, and starting at week 7, mice were treated with 12.5 mg/kg AA daily for three additional weeks. Mice were sacrificed at the end of week 9. Mice that were treated with AA from weeks 7-9 showed maximal improvement when compared to the control mice. The data are expressed as the mean pixel intensity of LFB staining normalized to controls measured at two non-overlapping regions of the corpus callosum.

At the end of weeks 7 and 8, mice that had received either one or two weeks of treatment with anacardic acid showed no differences in the expression of myelin when compared to the corresponding control mice. However, at the end of week 9, mice that had received three weeks of AA showed a significant increase in the amount of myelin staining of the corpus callosum as compared to the corresponding control mice. There was a 10% increase in LFB staining (sum of 12 different regions from 6 mice) in AA treated mice as compared to control mice (P<0.02) (FIG. 10).

Figure 11:
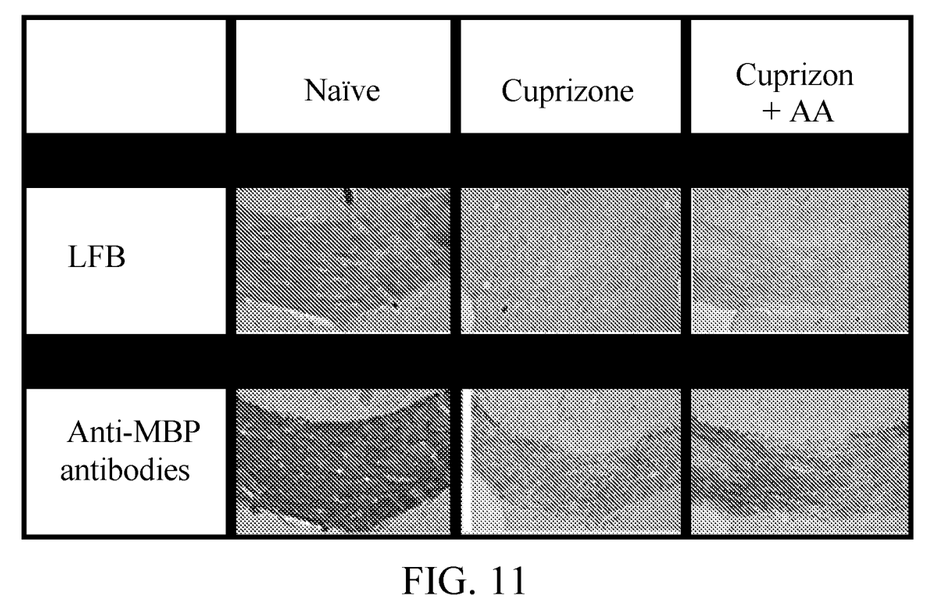
FIG. 11 provides images showing the staining of myelin using LFB stain (top panel) and immunostaining with anti MBP antibodies (bottom panel) in coronal sections of the brain in a 9-week study of naïve (left), cuprizone treated (middle), and cuprizone+AA treated (12.5 mg/kg/day) mice where the cuprizone+AA treated mice were treated with AA in weeks 7-9 of the study. The Y axis represents the mean pixel intensity of staining normalized to controls for LFB and immunostaining for MBP.
Figure 12:
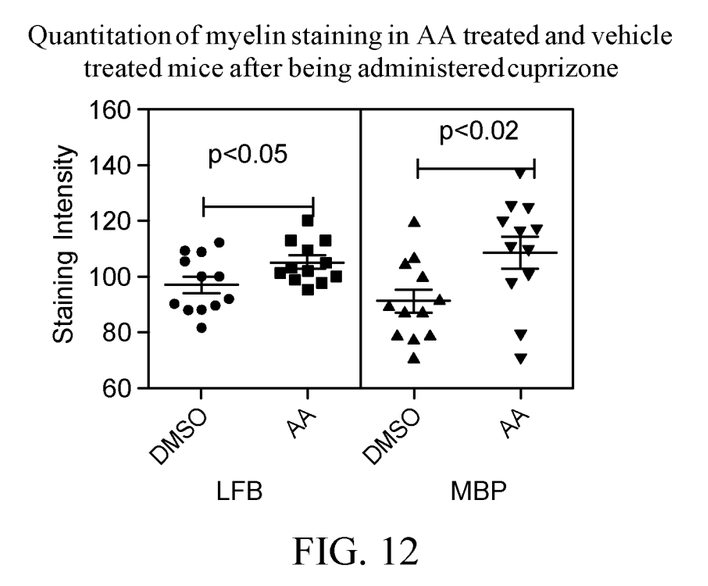
FIG. 12 shows the quantitation of myelin staining using LFB stain (left) and immunostaining with anti MBP antibodies (right) in coronal sections of the corpus callosum in AA treated (12.5 mg/kg/day) and vehicle treated mice after being administered cuprizone for 9 weeks and being administered AA during weeks 7-9 of the study. Higher amounts of myelin were seen in the AA treated mice as compared to the control mice.

Additional immunostaining with anti MBP antibodies was also conducted. It was found that there was a 17% increase in MBP staining in AA treated mice as compared to control mice (P=0.02). There was no difference in the number of oligodendrocytes present between anacardic acid and vehicle treated mice. This would therefore suggest that the anacardic acid was most likely increasing the differentiation of immature oligodendrocytes to mature forms even in the presence of a gliotoxic agent (FIG. 11 and FIG. 12).

(viii) AA is Effective in Preventing and Reversing the Course of Acute Experimental Allergic Encephalitis.

Experimental allergic encephalitis ("EAE") is an autoimmune inflammatory demyelinating disease of the CNS. For experimental purposes, the disease is induced in animals by immunizing the animals with myelin antigens in adjuvant. Traditionally, the neural antigen is myelin oligodendrocyte protein (MOG) or synthesized peptides of the MOG (peptide P35-55), which have been shown to be encephalitogenic. Ten to twelve days after immunization, paralysis develops in the animals. The degree of paralysis is scored as follows:

1=limp tail, 2=ataxia of gait and paralysis of one or more limbs, 3=paralysis of two or more limbs, 4=weakness of all limbs, 5=death.

The EAE model has been used extensively to examine the efficacy of potential drugs for MS therapy. The efficacy of AA in preventing EAE in mice immunized with MOG peptide in adjuvant was tested. A total of 10 mice were administered 0.25 mg/kg of AA dissolved in DMSO (vehicle) and a total of 10 mice were administered the vehicle alone by intraperitoneal injection daily for the entire length of the study (28 days). AA was obtained from commercial sources. Nine of 10 animals in the vehicle group developed paralytic signs, with a mean maximal paralytic score of 2.66. Two of 10 animals that received AA developed paralysis which was scored as a grade 1 paralysis (P<0.01 treated versus placebo). There was also significant decrease in the loss of myelin in the vehicle treated group when compared to the mice that were treated AA. (FIG. 13).

Figure 13:
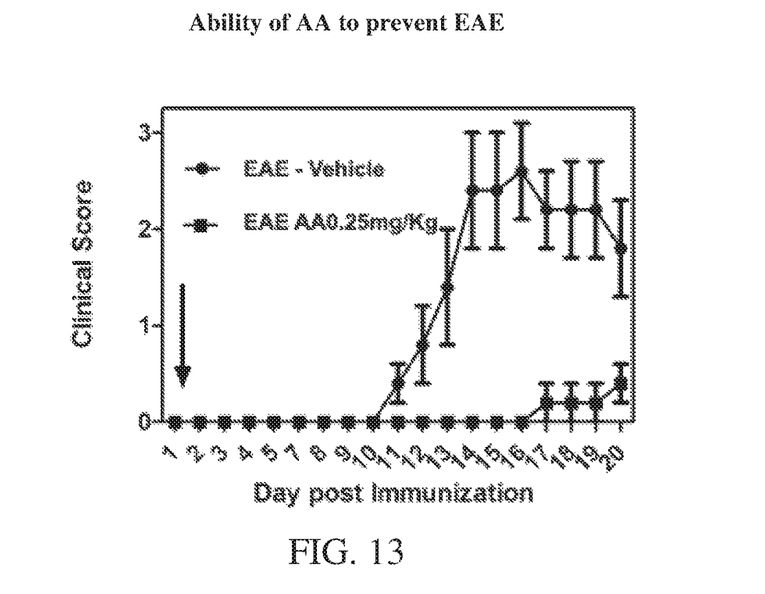
FIG. 13 demonstrates the ability of AA to prevent EAE in mice that were immunized with MOG peptide and treated with AA (0.25 mg/kg/day). In two experiments, only 2 of 10 mice in the AA treated group developed grade 1 paralysis. In the vehicle treated group, 9 out of 10 mice developed paralysis. Clinical scoring: 1=limp tail, 2=ataxia of gait and paralysis of one or more limbs, 3=paralysis of two or more limbs, 4=weakness of all limbs, 5=death.
Figure 14:
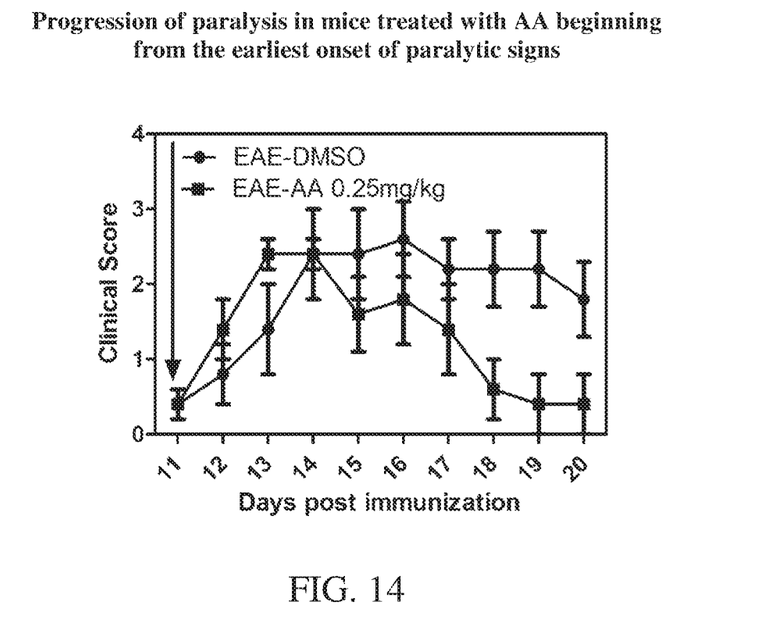
FIG. 14 shows the progression of paralysis in mice treated with AA (0.25 mg/kg/day) beginning from the earliest onset of paralytic signs. The mice that received treatment with AA exhibited a more rapid recovery.

To determine if treatment with AA would promote recovery after paralytic attack, the experiment shown in FIG. 13 was repeated but treatment with AA was not initiated until the earliest sign of disease appeared which occurred between days 11 and 12 following the initial immunization with MOG antigen. In the experiment, 10 mice were administered 0.25 mg/kg AA a day in DMSO and 10 mice were administered DMSO (vehicle). In the 10 mice that received 0.25 mg/kg AA a day, there was no difference in the mean maximal severity of the disease when compared to vehicle treated mice. The mean maximal severity was 2.8 in the vehicle treated group and was 2.6 in the AA treated group. However, there was a rapid reversal of paralysis in the AA treated group. By day 24, with the exception of one animal in the AA treated group which showed a grade 2 weakness, all the other mice had fully recovered. In comparison, 6 of 10 mice in the vehicle group still exhibited states of paralysis with a mean clinical score of 1.8 (FIG. 14).

To confirm that the clinical scores calculated in the EAR experiments reflect pathology, the extent of demyelination in the cervical, thoracolumbar cord of each mouse in the vehicle treated and AA treated groups was examined. In the group that was treated with 0.25 mg/kg AA daily beginning from the day of immunization, the mean percent of demyelination in the vehicle treated group was 9.9+/−4.0. The mean maximal clinical score in this group was 2.7. In the mice that received 0.25 mg/kg AA daily from day 0, no demyelination was seen suggesting a complete pathological protection.

Figure 15:
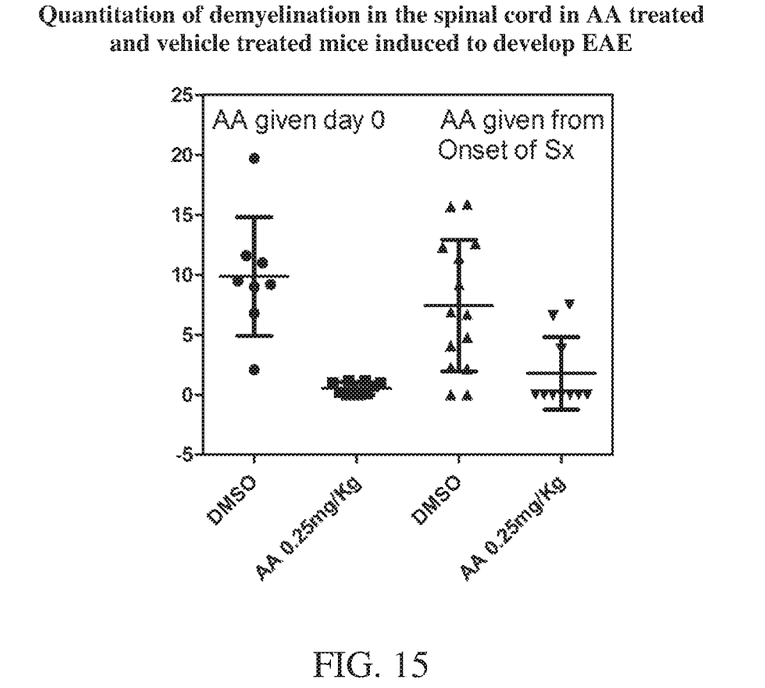
FIG. 15 shows the quantitation of demyelination in the spinal cord in AA treated (0.25 mg/kg/day) and vehicle treated mice induced to develop EAE. The data shows that there was significant protection from demyelination in the mice that were treated with AA. The data is expressed as a percent area of myelin loss in three non-contiguous axial sections of the spinal cord; $p<0.01$ between treated and untreated groups when AA is given beginning day 0 or from the onset of symptoms.

When AA was administered at the earliest onset of clinical signs of paralysis, the percent demyelination score in the AA treated group was 2.9. In comparison, in the vehicle treated group the percent demyelination score was 7.2 (P<0.01) (FIG. 15).

The complete disclosure of all patents, patent applications, and publications, and electronically available materials cited herein are incorporated by reference. All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls. The foregoing detailed description and examples have been given for clarity of understanding only. No unnecessary limitations are to be understood therefrom. In particular, while various theories are presented describing possible mechanisms through with the compounds are effective, the compounds are effective regardless of the particular mechanism employed and the inventors are therefore not bound by theories described herein. The disclosure is not limited to the exact details shown and described, for variations obvious to one skilled in the art will be included within the disclosure defined by the claims.

What is claimed is:

1. A method of stimulating neural repair in a subject in need thereof, wherein the method comprises administering to the subject an effective amount of anacardic acid (AA) having the structure:

AA or a pharmaceutically acceptable salt thereof.

2. The method of claim 1, wherein AA is administered to the subject.

3. The method of claim 1, wherein the subject has been diagnosed as having a demyelinating disorder.

4. The method of claim 2, wherein the demyelinating disorder is multiple sclerosis.

5. The method of claim 1, wherein the subject has been diagnosed as having an infection causing demyelination.

6. The method of claim 1, wherein AA is administered with a pharmaceutically acceptable carrier.

7. The method of claim 1, wherein the effective amount of AA that is administered is between 250-1500 mg AA a day.

8. A method of stimulating remyelination in a subject in need thereof, wherein the method comprises administering to the subject an effective amount of AA or a pharmaceutically acceptable salt thereof.

9. The method of claim 8, wherein the subject has been diagnosed as having a demyelinating disorder.

10. The method of claim 9, wherein the demyelinating disorder is multiple sclerosis.

11. The method of claim 8, wherein the subject has been diagnosed as having an infection causing demyelination.

12. The method of claim 11, wherein the infection causing demyelination is human immunodeficiency virus infection.

13. The method of claim 8, wherein AA is administered with a pharmaceutically acceptable carrier.

14. The method of claim 8, wherein the effective amount of AA that is administered is between 250-1500 mg AA a day.

15. A method of treating a myelin related disorder in a subject in need thereof, comprising administering to the subject an effective amount of AA or a pharmaceutically acceptable salt thereof.

16. The method of claim 15, wherein the myelin related disorder is multiple sclerosis.

17. The method of claim 15, wherein the myelin related disorder is an injury to the spinal cord.

18. The method of claim 15, wherein the myelin related disorder is a cerebral infarction.

19. The method of claim 15, wherein the myelin related disorder is post-infectious encephalomyelitis.

20. The method of claim 15, wherein the effective amount of AA that is administered is between 250-1500 mg AA a day.

* * * * *